Figure 3:
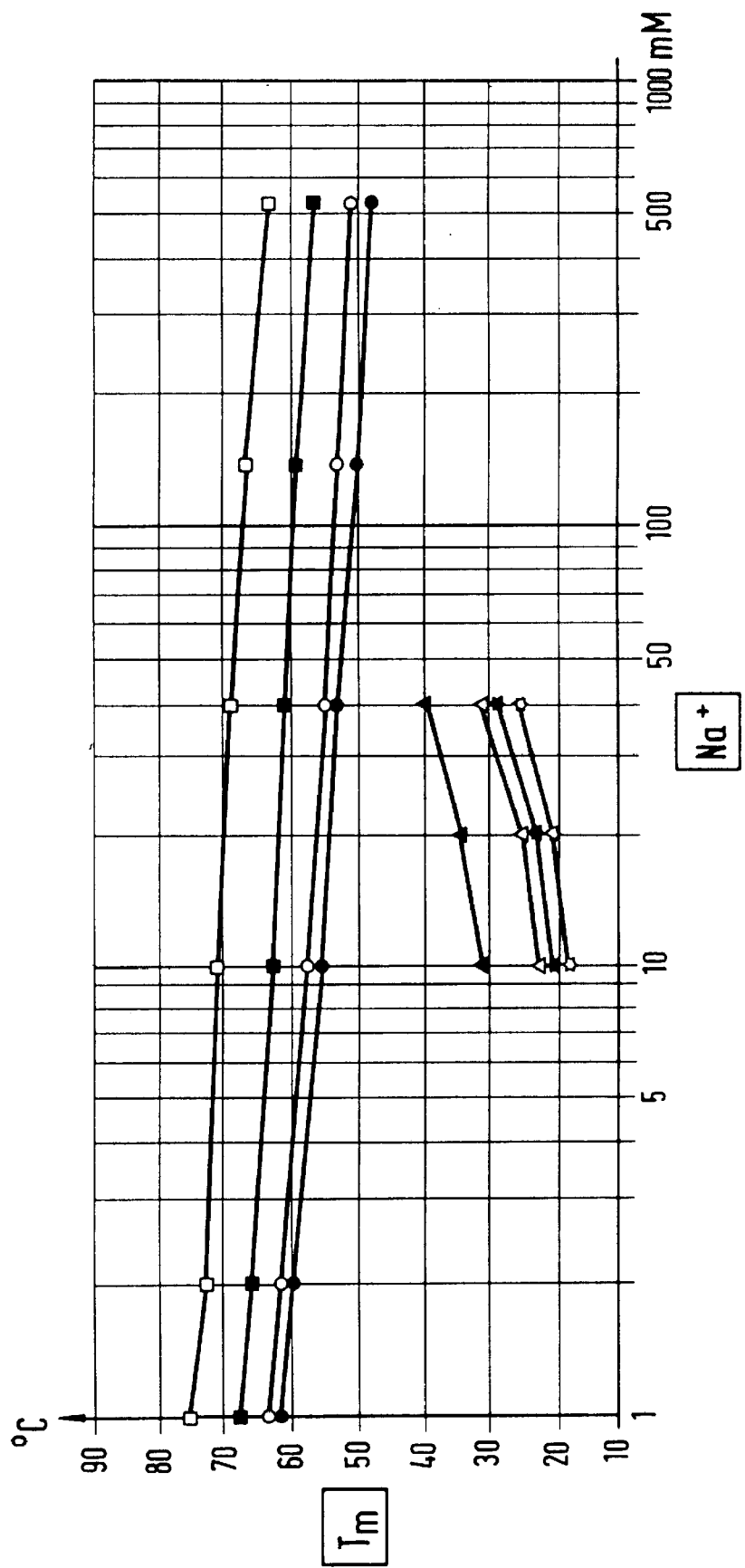

United States Patent [19]
Stanley et al.

[11] Patent Number: 5,843,663
[45] Date of Patent: Dec. 1, 1998

[54] METHODS OF CAPTURING NUCLEIC ACID ANALOGS AND NUCLEIC ACIDS ON A SOLID SUPPORT

[75] Inventors: Christopher John Stanley, Huntingdon, Great Britain; Henrik Orum, Vaerlose; Mikkel Jorgensen, Glostrup, both of Denmark

[73] Assignee: Boehringer Mannheim GmbH, Mannheim, Germany

[21] Appl. No.: 653,607

[22] Filed: May 24, 1996

Related U.S. Application Data

[63] Continuation-in-part of PCT/EP94/03859, Nov. 22, 1994.

[30] Foreign Application Priority Data

Nov. 25, 1993 [GB] United Kingdom ............... 9324243.6

[51] Int. Cl.$^6$ ............................................ C12Q 1/68
[52] U.S. Cl. ............................. 435/6; 436/501; 530/300; 530/350; 935/77; 935/78
[58] Field of Search ..................... 435/6, 810; 436/501; 530/300, 350; 536/23.1, 24.1, 24.3–33; 935/77, 78

[56] References Cited

U.S. PATENT DOCUMENTS 5,571,940  11/1996  Palacios ................................. 562/556

Primary Examiner—Ardin H. Marschel
Attorney, Agent, or Firm—Nikaido Marmelstein Murray & Oram LLP

[57] ABSTRACT

A nucleic acid analog comprising a polymeric strand which includes a sequence of ligands bounds to a backbone made up of linked backbone moieties, which analog is capable of hybridization to a nucleic acid of complementary sequence, further comprising a chelating moiety capable of binding at least one metal ion by chelation.

39 Claims, 7 Drawing Sheets

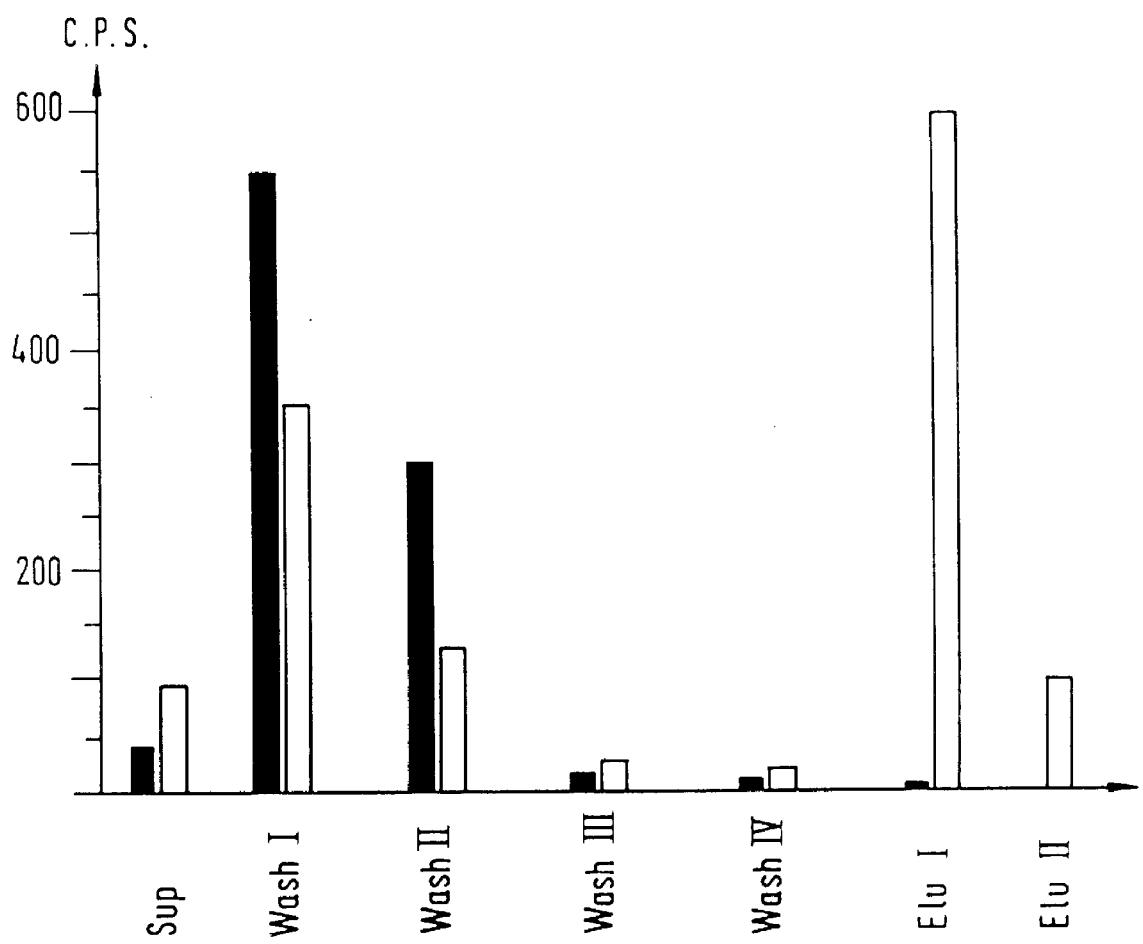

Fig. 2

| PNA/DNA COMPLEX | Mismatch | X = none | X = ado$_3$ | X=ado$_3$-His$_6$ |
|---|---|---|---|---|
| 5'-CTAGAGGATCTAGTTGTGTGACGTACAGGATCTTTTTCATAG-3'<br>PNA: H$_2$N-ATCAACACTGCATGT-X | None | 64.2 °C | 65.2 °C | 63.6 °C |
| 5'-CTAGAGGATCTAGTTGTGTGAAGTACAGGATCTTTTTCATAG-3'<br>PNA: H$_2$N-ATCAACACTGCATGT-X | G$_{PNA}$/A$_{DNA}$ | 49.0 °C | 49.6 °C | 47.4 °C |
| 5'-CTAGAGGATCTAGTTGTGTGATGTACAGGATCTTTTTCATAG-3'<br>PNA: H$_2$N-ATCAACACTGCACGT-X | G$_{PNA}$/T$_{DNA}$ | 56.4 °C | 57.8 °C | 56.2 °C |
| 5'-CTAGAGG ATCTAGTTGTGTGAGGTACAGGATCTTTTTCATAG-3'<br>PNA: H$_2$N-ATCAACACTGCATGT-X | G$_{PNA}$/G$_{DNA}$ | 50.0 °C | 51.6 °C | 50.6 °C |

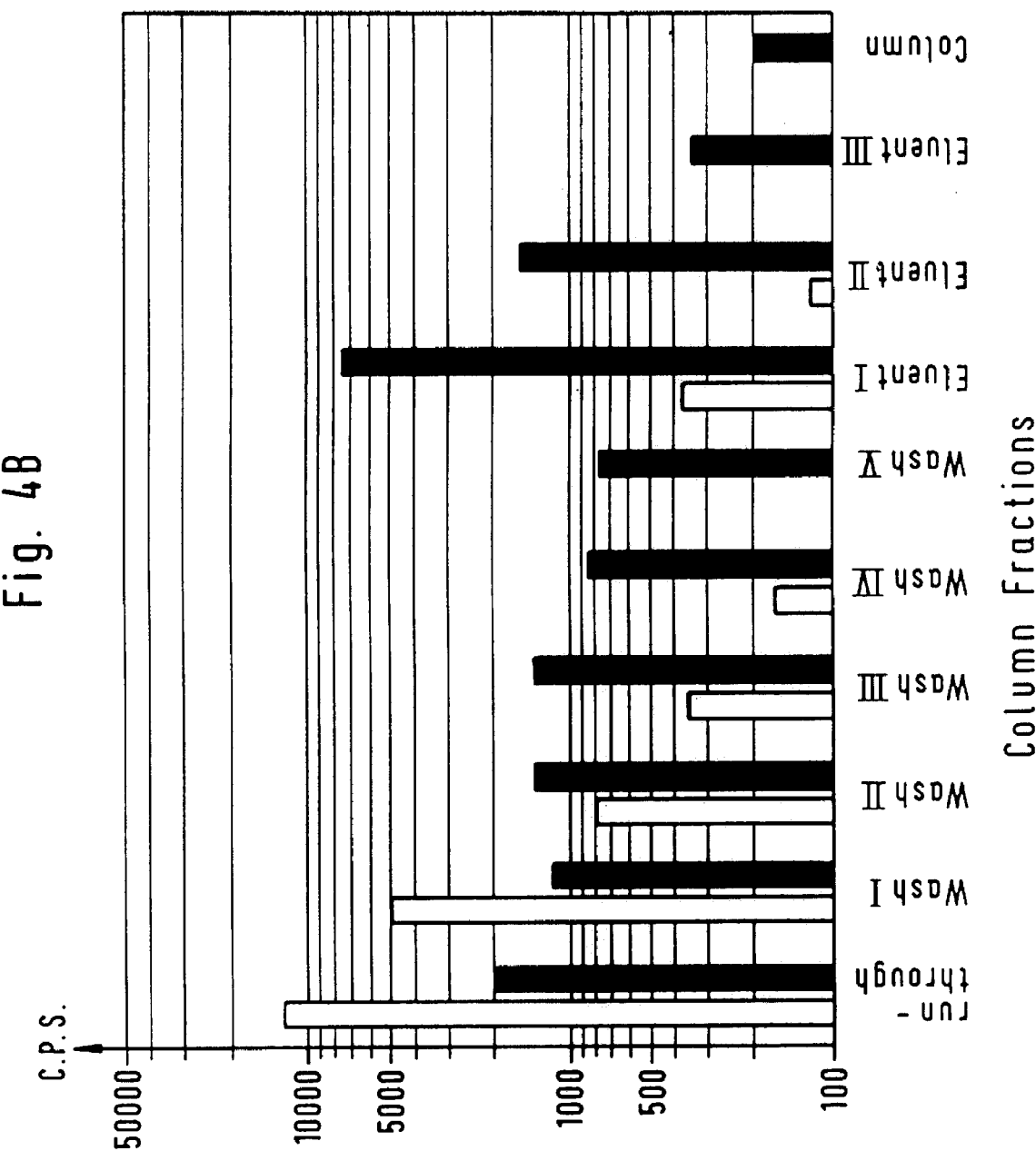
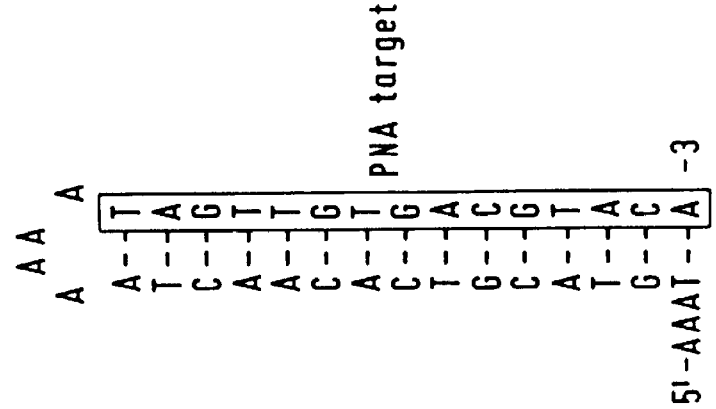
Fig. 4B
Fig. 4A

Fig. 6B

| Row | Transcript size | PNA | Size of PNA segment | % in eluent | %Remaining on column |
|---|---|---|---|---|---|
| 1 | 290 nt. | 111 | 15 mer | 2.0 | 1.0 |
| 2 | 290 nt. | 113 | 20 mer | 1.7 | 0.6 |
| 3 | 257 nt. | none | - | 1.4 | 0.1 |
| 4 | 257 nt | 111 | 15 mer | 44.0 | 0.7 |
| 5 | 257 nt. | 133 | 16 mer | 45.2 | 0.8 |
| 6 | 257 nt | 111, 133 | - | 57.4 | 0.7 |
| 7 | 2224 nt. | none | - | 3.7 | 1.7 |
| 8 | 2224 nt. | 111 | 15 mer | 25.0 | 2.6 |
| 9 | 2224 nt. | 113 | 20 mer | 26.7 | 3.3 |
| 10 | 2224 nt. | 153 | 15 mer | 38.3 | 1.9 |
| 11 | 2224 nt. | 154 | 15 mer | 22.1 | 1.4 |
| 12 | 2224 nt. | 111, 153 | - | 53.1 | 3.9 |
| 13 | 2224 nt | 111, 154 | - | 47.7 | 3.5 |
| 14 | 2224 nt | 153, 154 | - | 50.9 | 4.1 |
| 15 | 2224 nt | 111, 153, 154 | - | 64.9 | 3.8 |

METHODS OF CAPTURING NUCLEIC ACID ANALOGS AND NUCLEIC ACIDS ON A SOLID SUPPORT

CROSS REFERENCE TO RELATED APPLICATION

This application is a continuation-in-part of International Application PCT/EP94/03859, filed Nov. 22, 1994, and designating the U.S.

The present invention relates to nucleic acid analogs having a chelation functionality, to their uses in assay procedures, to methods of capturing them to solid supports and to methods of concentrating solutions of them.

Nucleic acid analogs having important new utilities in assay procedures and in the field of diagnostics have been described in WO 92/20703. These nucleic acid analogs had a number of new properties making them of special importance in the field of diagnostics as well as in the field of antisense therapeutics.

They typically feature a polyamide backbone bearing a sequence of ligands which are nucleic acid bases. The analogs described there have the property of hybridizing with great specificity and stability to natural nucleic acids of complementary sequence.

In order to aid the detection and the manipulation of such nucleic acid analogs in diagnostics or other assay procedures and the like operations, it is desirable to provide the nucleic acid analogs with detectable labels. It is also desirable to find ways of capturing said nucleic acid analogs on solid supports. Various labels are described in WO 92/20703. Also, the capture of the nucleic acid analogs to solid supports via bound nucleic acid or nucleic acid analog sequences acting as capture probes is described However, it is desirable to find alternative capture methods and in particular methods which do not require a tailored capture probe which is sequence specific but rather are generally applicable to such nucleic acid analogs.

In EP-A-0 097 373 the synthesis of nucleic acids labeled with a complexing agent is described. However, the synthesis of these compounds appears to be complicated Furthermore, whilst natural nucleic acids are readily and routinely concentrated by precipitation from solution by ethanol, centrifugation and resuspension, no such convenient method presently exists to aid those working with these nucleic acid analogs.

The present invention now provides according to a first aspect thereof a nucleic acid analog comprising a polymeric strand which includes a sequence of ligands bound to a backbone made up of linked backbone moieties, which analog is capable of hybridization to a nucleic acid of complementary sequence, further comprising, preferably at one terminus of said backbone a chelating moiety capable of binding at least one metal ion by chelation.

Preferably, the backbone is a polyamide, polythioamide, polysulphinamide or polysulphonamide backbone and preferably said chelating moiety is present at the N-terminus.

The chelating moiety preferably comprises a sequence of peptide bonded amino acids.

Preferred sequences of amino acids for use as chelating moieties are -His, Gly,Asp or -(His)$_n$, where n=3 to 10, e.g. 5 or 6. The longer sequences may bind more than one metal ion per molecule of nucleic acid analog.

Alternatively, said chelating moiety may be a polycarboxylic acid substituted amine such as ethylenediaminetetraacetic acid (EDTA) or aminotriacetic acid (NTA) and the like.

The nucleic acid analog is preferably capable of hybridizing to a nucleic acid of complementary sequence to form a hybrid which is more stable against denaturation by heat than a hybrid between the conventional deoxyribonucleotide corresponding in sequence to said analog and said nucleic acid.

Said nucleic acid analog is preferably a peptide nucleic acid in which said backbone is a polyamide backbone, each said ligand being bonded directly or indirectly to a nitrogen atom in said backbone, and said ligand bearing nitrogen atoms mainly being separated from one another in said backbone by from 4 to 8 intervening atoms.

The analog is preferably capable of hybridizing to a double stranded nucleic acid in which one strand has a sequence complementary to said analog, in such a way as to displace the other strand from said one strand.

More preferred PNA compounds for use in the invention have the formula:

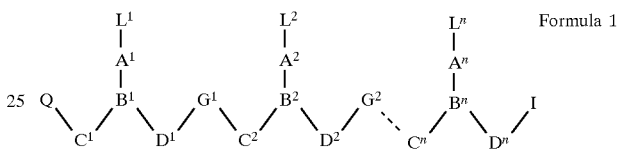

Formula 1 n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, reporter ligands and chelating moieties;

each of $C^1$–$C^n$ is $(CR^6R^7)y$ preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined below, and $R^5$ is hydrogen, ($C_1$–$C_6$)alkyl, hydroxy, alkoxy, or alkylthio-substituted ($C_1$ to $C_6$)alkyl or $R^6$ and $R^7$ taken together complete an alicyclic or heterocyclic system;

each of $D^1$–$D^n$ is $(CR^6R^7)_z$ (preferably $CR^6R^7$, $CHR^6CHR^7$ or $CH_2 CR^6R^7$) where $R^6$ and $R^7$ are as defined above;

each of y and z is zero or an integer from 1 to 10, the sum y+z being at least 2, preferably greater than 2, but not more than 10;

each of $G^1$–$G^{n-1}$ is —$NR^3CO$—, —$NR^3C^5$—, —$NR^3SO$— or —$NR^3SO_2$—, in other orientation, where $R^3$ is as defined below;

each of $A^1$–$A^n$ and $B^1$–$B^n$ are selected such that:
(a) A is a group of formula (IIa), (IIb), (IIc) or (IId), and B is N or $R^3N^+$; or
(b) A is a group of formula (IId) and B is CH;

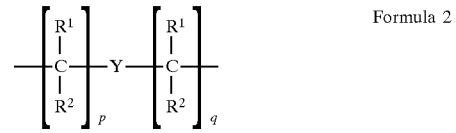

Formula 2

-continued

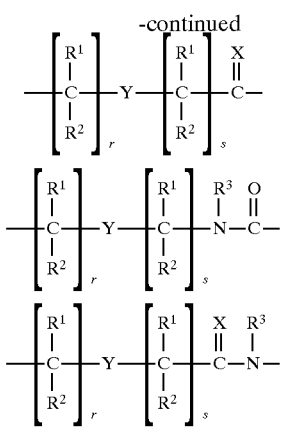

Formula IIb

Formula IIc

Formula IId wherein:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1–C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1–C_4)$alkyl hydroxy- or alkoxy- or alkylthio-substituted $(C_1–C_4)$alkyl, hydroxy, alkoxy, alkylthio and amino;

Q is $—CO_2H$, $—CONR'R''$, $—SO_3H$ or $—SO_2—NR'R''$ or an activated derivative of $—CO_2H$ or $—SO_3H$; and I is $—NR'R'''$ where R' and R'' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers, and $—R'''$ is a chelating moiety. "Oligonucleosides" includes nucleobases bonded to ribose and connected via a backbone other than the normal phosphate backbone of nucleic acids.

In the above structures wherein R' or R'' is an oligonucleotide or oligonucleoside, such structures can be considered chimeric structures between PNA compounds and the oligonucleotide or oligonucleoside.

Generally, at least one of $L^1–L^n$ will be a naturally occurring nucleobase, a non-naturally occurring nucleobase, a DNA intercalator, or a nucleobase binding group.

Preferred PNA-containing compounds useful to effect binding to RNA, ssDNA and dsDNA and to form triplexing structures are compounds of the formula III, IV or V:

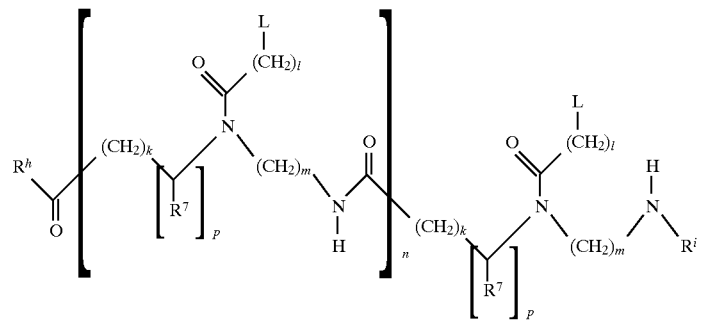

Formula III

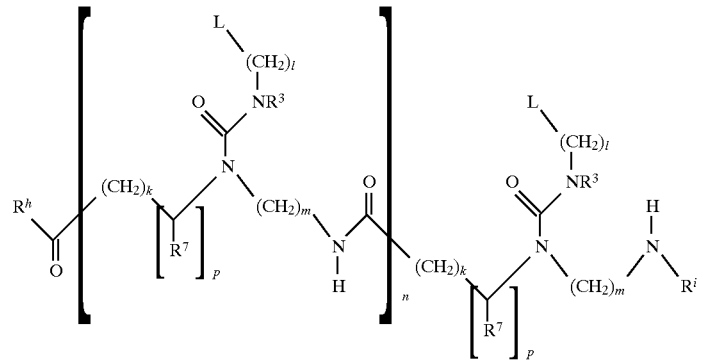

Formula IV

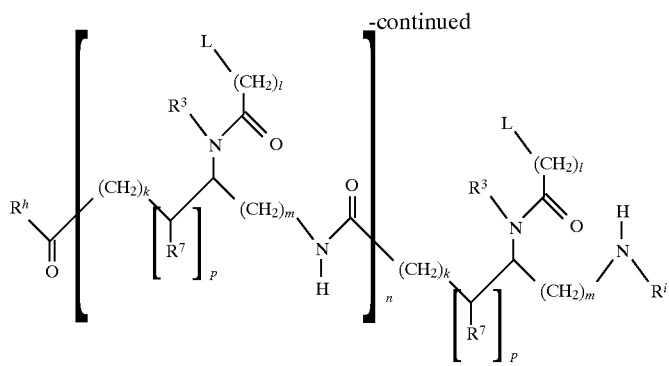

Formula V wherein:
- each L is independently selected from the group consisting of hydrogen, phenyl, heterocyclic moieties, naturally occurring nucleobases, and non-naturally occurring nucleobases;
- each $R^7$ is independently selected from the group consisting of hydrogen and the side chains of naturally occurring alpha amino acids;
- n is an integer greater than 1,
- each k, l, and m is, independently, zero or an integer from 1 to 5;
- each p is zero or 1;
- $R^h$ is OH, $NH_2$ or —$NHLysNH_2$; and
- $R^i$ is a chelating moiety.

The invention includes according to a second aspect thereof a method of capturing a nucleic acid analog of the kind described above, which method comprises exposing the nucleic acid analog to a solid support bearing chelatable metal ions bonded thereto under conditions such that the chelating moiety of the nucleic acid analog chelates the said bound metal ions, so capturing the nucleic acid analog to the solid support.

Alternatively, the capture process may comprise exposing the nucleic acid analog and chelatable metal ions to a solid support capable of binding the metal ions under conditions such that the metal ions become bound to the solid support and chelated by the chelating moiety of the nucleic acid analog. The metal ions can if preferred be chelated by the nucleic acid analog or to the solid support prior to the nucleic acid analog and the solid support being exposed to one another.

The solid support may comprise a chelating agent such as NTA or EDTA bound thereto chelating ions such as nickel or copper ions which are further chelatable by said nucleic acid analog.

A particularly preferred solid support is agarose gel and the solid support bearing chelatable metal ions may preferably be Ni-NTA-agarose. Conveniently, the gel may be in a column through which a solution containing the nucleic acid analog to be captured may be passed, e.g. a spin column through which said solution is centrifuged. Another preferred form of solid support is magnetic particles with a surface bearing chelatable metal ions, which may be held thereon by chelating agents as described above.

Such a method preferably comprises capturing said nucleic acid analog from a first volume of solution by a method as described, removing the solid support and captured nucleic acid analog from said solution and eluting the nucleic acid analog from the solid support in a quantity of liquid such as to produce a second volume of a solution of said nucleic acid analog which is less than said first volume of solution. The nucleic acid analog is thereby concentrated with respect to its starting solution concentration. The elution may be carried out with an excess of chelating agent such as EDTA.

A solid support having a nucleic acid analog bound thereto or capable of capturing such a nucleic acid analog by the techniques described above maybe used to capture from solution a nucleic acid of complementary sequence. A particular virtue of this technique is that one then has the option of removing the captured nucleic acid from the solid support either with or without the nucleic acid analog.

Thus by treating the system with an excess of a chelating agent such as EDTA, the chelated metal can be removed, so freeing the nucleic acid analog, and any hybridized nucleic acid. Alternatively, one may liberate the nucleic acid from the nucleic acid analog on the support by heat or other denaturing methods.

One example of such capture of a nucleic acid would be to hybridize a nucleic acid to the nucleic acid analog capture probe bearing a chelating moiety, and then to capture the resulting complex on a solid bearing metal ions.

When standard DNA probes are used in hybrid selection procedures one of the serious limitations is target sequence inaccessibility due to competing hybridization events. For instance, when targeting double-stranded PCR products the DNA probe competes with the complementary non-target PCR strand. Target sequence inaccessibility can also be caused by secondary and higher order structures in the target nucleic acid. Such structures are well characterized in the case of many metabolically stable RNAs (RNA, tRNA and snRNAs). We have shown that PNA can hybridize to its complementary nucleic acid over a broad range of salt concentrations without loss of affinity and specificity. In fact the affinity of the PNA increases as the salt concentration in the buffer decreases. In theory, this is a most useful property of PNA as it allows hybridization to its target sequence under conditions of low salt that destabilizes normal nucleic acid structures. We have provided an example that this property of PNA can be used to capture a "difficult" oligonucleotide in which the PNA target sequence is designed to form one side of an intra-molecular, perfectly matched 15 bp stem structure.

Methods that facilitate the rapid purification of nucleic acids from complex biological samples are important tools in both basic research and in DNA diagnostics. Compared to methods that rely on physical properties of the nucleic acids for purification, such as density, binding to surfaces, solubility, the hybrid selection method described here offers two main advantages. Firstly, it utilizes a property that is unique to nucleic acids—namely the ability to hybridize to a probe of complementary sequence. Hence, the chance of copurification of other cellular components that may prove inhibitory to downstream applications are likely to be minimal. Secondly, the method allows specific nucleic acids to be targeted thereby removing bulk DNA and RNA that may add to the generation of non-specific background in subsequent target detection procedures.

The invention includes in a third aspect thereof a labeled nucleic acid analog comprising a nucleic acid analog according to the first aspect of the invention, having chelated thereto via said chelating moiety a metal ion as label or having a labeling moiety linked thereto via a metal ion chelated by said chelating moiety. Said metal ion is preferably a radio label such as $^{111}$indium or $^{99}$technetium or a fluorescent label such as europium or terbium.

The compounds and methods of a present invention provide a very rapid method for analyzing nucleic acids. The hybridization with the compounds of the invention can be used to define very efficient assays with a great specificity. The use of low salt conditions provides a method for analyzing even nucleic acids containing stem loop structures. It further allows the separation of nucleic acids differing by only one nucleotide. The compounds are very easy to prepare because peptide chemistry can be used to couple the complexing agent to the back bone.

Further the present compounds can be used efficiently as labeled probes in the analysis of PCR products, because they compete very efficiently with the counter strands. Further the compounds of the present invention show the superior property that also large RNAs can be captured and/or determined.

Nucleic acid analogs according to the first aspect of the invention may be prepared by first synthesizing a PNA by the solid phase techniques described in WO 92/20703 to produce a Boc-terminated PNA bound to a solid support at its carboxy end. The PNA may then be extended by removal of the Boc group to yield a starting point for a standard boc type or Fmoc type solid phase peptide synthesis adding for instance the required chelating amino acids via the linker 6-aminohexanoic acid. The protection groups may then be removed and the product may be cleaved from the resin by the Low-High TFMSA procedure. The raw product may be purified by preparative HPLC (suitable conditions being: reversed phase $C_{18}$ eluting with a gradient of A: 0.1% TFA in water and B: 0.1%, 10% water, 89% acetonitrile).

The invention will be illustrated by the following examples making reference to the accompanying drawing in which:

FIG. 1 is a bar graph showing the radioactivity counts obtained in the measurements described in Example 1.

In FIG. 2 the flexibility of the PNA construction is shown with respect to linkers or tags.

FIG. 3 shows the dependence of the melting curves from the concentration of sodium ions.

FIG. 4A shows the sequence of an intramolecular stem structure of an oligonucleotide. The PNA target site is marked. In FIG. 4B the results of retention experiments under different salt conditions is shown.

Figure 5:
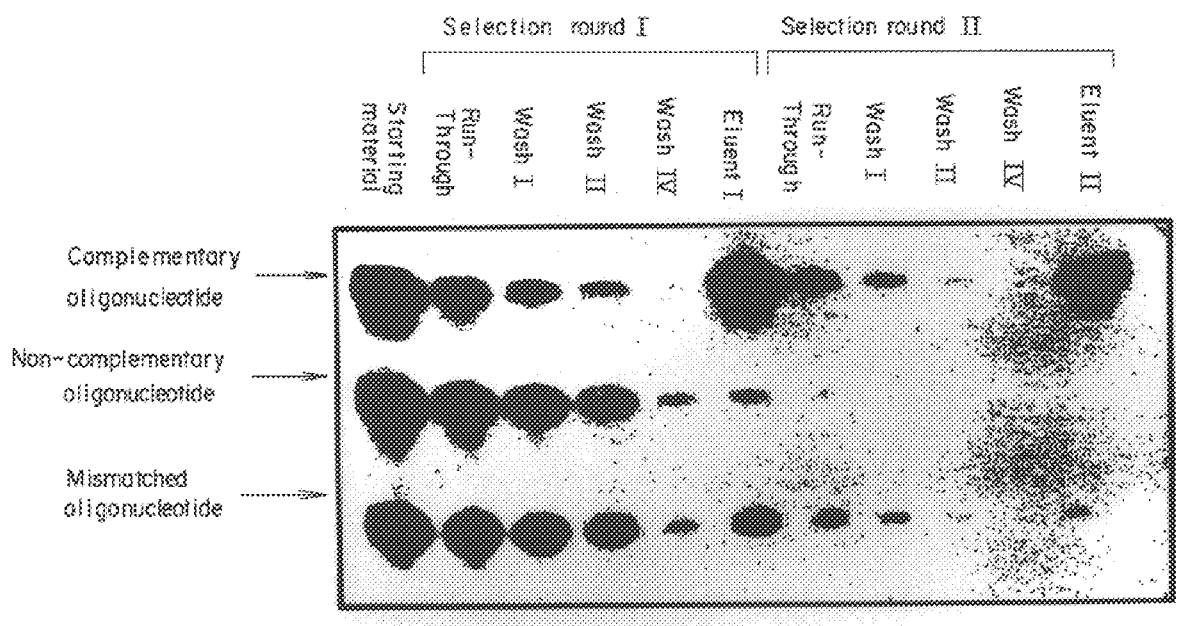

In FIG. 5 the efficiency of the capture of oligonucleotides by PNAs is shown.

Figure 6A:
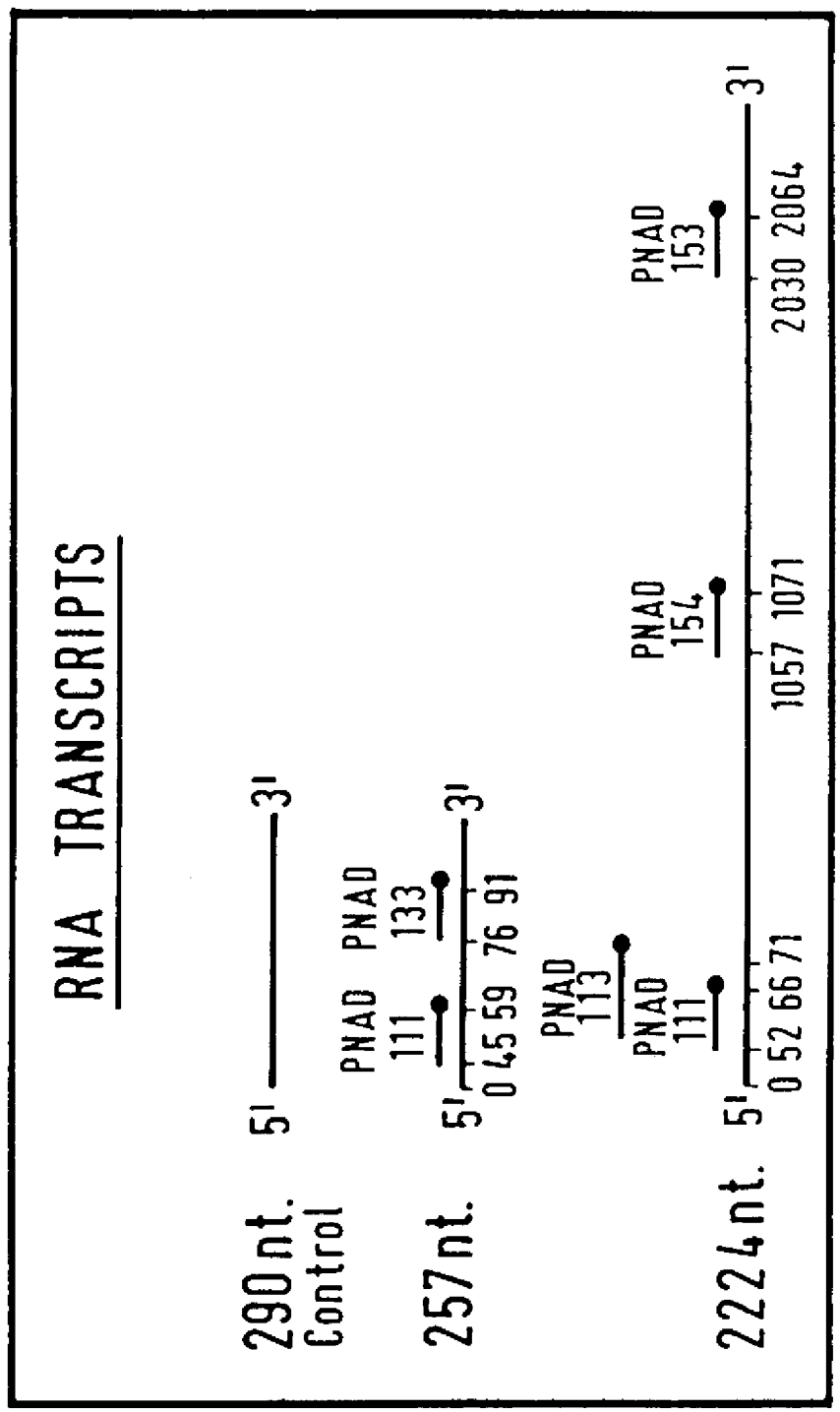

In FIG. 6 the specificity of the capture of in-vitro generated RNAs by PNA is shown.

In the following examples, the PNA used has an aminoethylglycine backbone and is prepared by the methods specifically described in WO 92/20703. The nomenclature used there in respect of PNAs is used here also.

EXAMPLE 1

Selective purification of DNA by immobilized histidine tagged PNA

The PNA:
Boc-NH-TG(Z)T.A(Z)C(Z)G(Z).TC(Z)A(Z).C(Z)A(Z)A(Z).C(Z)TA(Z)-CONH-Resin
was constructed. This was extended to the tagged PNA:
H-His5-NH(CH$_2$)$_5$CONH-TGTACGTCACAACTA-NH$_2$
as follows:

The protected PNA on MBHA resin was coupled with the 6-amino-hexanoic acid linker by boc type solid phase synthesis.

After boc deprotection of the amino terminus, the His$_5$ motif was built up using an Fmoc strategy. Fmoc-His(Trt)-OH was coupled 2×1 h with diisopropylcarbodiimide in DCM/DMF. The Fmoc group was cleaved by treatment with 20% piperidine in DMF (1×5 min and 1×10 min).Coupling and Fmoc deprotection were repeated another four times. The trityl protection groups were removed by 50% TFA in DCM (2×30 min). Finally the Z groups were removed and the product cleaved from resin by standard HP procedure. The raw product was purified by preparative HPLC.

The tagged PNA was incubated with either complementary or non-complementary, $^{32}$P labeled oligonucleotides in a 20 µl reaction volume containing 20 mM NaH$_2$PO$_4$ (pH 8.0) 0.5M NaCl. Incubation was carried out at room temperature for 15 min. At the end of the incubation period 180 µl of buffer 1 (20 mM NaH$_2$PO$_4$ (pH 8.0) 0.5M NaCl) was added and the reaction mixture was loaded onto a Duraphore™ 0.22 µM spin column (Mllipore) packed with 200 µl Ni-NTA-agarose (Pharmacia).The column was centrifuged for 30 seconds at 1000 rpm and the radioactivity in the flow through (named Sup) was counted using a Geiger Muller tube.

The column was washed three times with 200 µl of buffer 1, and the radioactivity in the flow through (named: Wash I-IV) was counted. The column was loaded with 200 µl of buffer 1, incubated at 95° C. for 5 min, and centrifuged for 30 seconds at 1000 rpm. The radioactivity in the flow through (named Elu I-II) was counted.

The results are shown in FIG. 1. As shown, the non-complementary oligonucleotides (black bars) are all lost from the column during the initial washing steps whereas the complementary oligonucleotide (white bars) remains on the column until the binding to the PNA is broken by heat denaturation. Thus, it is shown that PNA carrying a His$_5$ tag can function as an effective tool in the purification of nucleic acids containing complementary targets.

EXAMPLE 2

Europium labeling of PNA by chelation

A PNA oligomer ("oligomer 1") was constructed having the sequence
Ado-TGT.ACG.TCACAACTA
where "Ado" is the linker 8-amino-3,6-dioxa-octanoic acid linked via its carboxylic acid terminus to the amino terminus of the PNA sequence. The PNA oligomer 1 was built-up on MBHA resin (150 mg, loading: 0.1 mmol/g) using the solid phase synthesis methods described in WO 92/20703. The product cleaved from the resin. The PNA oligomer 1 (0.1 mg) was dissolved in 1 ml 50 mM NaHCO$_3$ buffer of pH 8.3 containing 0.9% NaCl and mixed with 0.2 mg of the europium salt of N-(4-isothiocyanate phenyl)-methyl-diethylene-triamine-N,N',N'', N''', tetra acetic acid. The labeling reaction was allowed to proceed for 16 hours at ambient temperatures and the product was purified by gel chromatography (G-25).

EXAMPLE 3
Alternative Europium labeling procedure

PNA-oligomer 1 was made as described in Example 2 but prior to cleavage from the resin the terminal amino group of the ado-linker was Boc deprotected with trifluoracetic acid and t coupled with diethylene triamine pentaacetic acid dianhydride (200 mg in 25 ml DMF). The product was cleaved from the resin by the standard TFMSA procedure and purified by reversed phase HPLC. The product was dissolved in water (1 mg/ml) and added to a 10 mM solution of europium chloride in water to form its europium complex. Excess europium chloride was removed by filtration through a Sephadex™ G-25 column.

EXAMPLE 4
General methods
Determination of melting temperatures ($T_m$) of PNA/DNA duplexes $_T$m value of PNA/DNA duplexes were determined spectrophotometrically at 260 nm in the indicated buffers containing 1.5 $\mu$M of PNA and 1.5 $\mu$M of DNA.

Synthesis of PNAs

Abbreviations and symbols used are standard oligopeptide/nucleotide nomenclature: H—: deprotected terminal amino group. —NH2: C-terminal amino group. Boc: tert-butylcarbonyl. Fmoc: 9-fluorenylmethyloxycarbonyl. HBTU: O-Benzotriacol-1-yl-N,N,N',N'-tetramethyluronium hexafluorophosphate. Ado: 8-amino-3.6-dioxa octanoic acid. Gly: glycine residue. PNA monomers. PNAD 153 ((His)$_6$-(ado)$_3$-TCTCAACAGCGGTAA-NH$_2$) and PNAD 154 ((His)6-(ado)3-GAAGGTAACTGGCTT-NH$_2$) were purchased from Biosearch (MA).

The following PNAs were synthesized: PNAD103 (H-TGTACGTCACAACTA-NH$_2$), PNAD 106 (H-(ado)$_3$-TGTACGTCACAACTA-NH$_2$), PNAD 111A ((His)$_6$-(ado)$_3$-TGTACGTCACAACTA-Gly-NH$_2$), PNAD113 ((His)$_6$-(ado)$_3$-GATCCTGTACGTCACAACTA-Gly-NH$_2$), PNAD133 ((His)$_6$-(ado)$_3$-GGCTGCAGGAATTCGA-Gly-NH$_2$), and derivatives of PNAD111 containing 3 from 3 to 8 histidine residues. The PNA segments including the ado linkers were synthesized manually by the improved solid phase PNA synthesis method which follows the Boc-strategy. Couplings were performed by adding HBTU to the PNA monomers, and acetic anhydride was used as the capping agent. The Boc protecting groups were removed by adding TFA/m-Cresol (95/5). The histidine segments were synthesized using the Fmoc strategy and the molar ratio of Fmoc-His(Trt)-OH/diisopropylcarbodiimide was the same as the ratio of PNA monomers/HBTU during the PNA segment syntheses. DMF/DCM was used during couplings and deprotection was performed by adding 20% piperidine in DMF (2×10 min). During the polyhistidine synthesis couplings were not followed by capping. Finally, the trityl protection groups were removed by TFA treatment (3×30 min) and the PNAs were deprotected and cleaved from the resin by the standard low-high TFMSA procedure. The crude PNAs were purified by reversed phase HPLC.

Selection of target DNA

5 $\mu$l of the His-PNA probes (5 OD$_{260}$/ml) were mixed with 10 $\mu$l of $^{32}$P labeled DNA oligonucleotide (0.2 $\mu$M) or 10 $\mu$l of $^{32}$P labeled, in vitro transcribed RNA, 50 $\mu$l of 8M urea, 100 $\mu$l of selection buffer (20 mM, Na$_2$HPO$_4$) (pH 8.0), 500 mM NaCl and 0.1% Triton™ X-100) and 35 $\mu$l of water in an Eppendorf tube. The solution was heated to 95° C. for 5 min and incubated for 10 min in a heating block at the indicated temperature. Meanwhile, a 400 $\mu$l sample of Ni-NTA resin (Quiagen) was loaded onto an Eppendorf spin column (Durapore 0.45 $\mu$m; Millipore) and centrifuged at 200 rpm for 30 sec to remove the Ni-NTA storage buffer. The column was washed three times in 200 $\mu$l water and equilibrated in 200 $\mu$l selection buffer. At the end of the hybridization period the mixture was loaded onto the column and centrifuged at 200 rpm for 30 sec. The column was washed several times in 200 $\mu$l of selection buffer to remove non-specifically bound nucleic acids. Finally, the purified target nucleic acids were eluted from the column by 1) adding 200 $\mu$l of selection buffer to the column, 2) incubating the column in a heating block at 95° C. for 5 min and 3) centrifugation at 200 rpm for 30 sec.

Radioactivity in the column fractions was counted using either a Geiger-Muller counter or a scintillation counter. Where analysis was conducted by gel electrophoresis, the nucleic acid in the column fractions was precipitated by adding 5 $\mu$g of carrier tRNA, 1 volume of 4M ammonium acetate and 2 volumes of 96% ethanol. The precipitated nucleic acid was recovered by centrifugation at 20000 rpm for 30 min, dried under vacuum, redissolved in formamide loading buffer and loaded onto a 16% denaturating polyarcylamide gels. After electrophoresis the gels were exposed to autoradiography.

Labeling of oligonucleotides 20 pmol of oligonucleotides were radioactively labeled using $\gamma$-$^{32}$P ATP and T4 polynucleotide kinase as described. To remove unincorporated $\gamma$-$^{32}$P ATP the labeled oligonucleotides were precipitated by added 5 $\mu$g of carrier tRNA, 1 volume of 4M ammonium acetate and 2 volumes of 96% ethanol. The precipitated oligonucleotides were recovered by centrifugation, dried under vacuum and dissolved in 100 $\mu$l of water. Two precipitations were performed and the labeled oligonucleotides were dissolved in water.

in vitro RNA transcription

The plasmid (pd62KS-4) was constructed by cloning the complementary oligonucleotides (5'-TCGAGGCAACCGAATAGTTGTGACGTACATTT-TTTA-3'(SEQ ID No: 1) and 5'-AGCTTAAAAAATGTACGTCACAACTATTCGGTT-GCC-3') into the (SEQ ID No: 2) Bluescript KS™ + plasmid (Stratagene) digested with XhoI and HindIII. The plasmid was linearized with PvuII and used to prepare labelled, run-off RNA transcripts of 257 nt. and 290 nt. (control) using either T3 or T7 RNA polymerase and $\alpha$-$^{32}$P CTP as described in Sambrook et al. (1989). Molecular cloning, A Laboratory manual (2nd. Ed). Cold Spring Harbor Laboratory, Cold Spring Harbor, N.Y.

The plasmid (pd62KS-2) was constructed in two rounds of cloing. First, the complementary oligonucleotides (5'-GATCCTGTACGTCACAACTA-3'(SEQ ID No: 2) and 5'-GATCTAGTTGTGACGTACAG-3) (SEQ ID No: 4) were cloned into the Bluescript KS+ plasmid (Stratagene) digested with BamHI to produce the plasmid pd62KS. Second, the complementary oligonucleotides (5'-GATCCGGCAACCGG-3'(SEQ ID No: 5) and 5'-AATTCCGGTTGCGG-3') (SEQ ID No: 6) were cloned into pd62KS digested with BamHI and EcoRI to produce the plasmid pd62KS-2. The plasmid (pd62KS-2) was linearized with SspI and used to prepare a labelled, run-off RNA transcripts of 2224 nt. using T7 RNA polymerase and $\alpha$-$^{32}$P CTP. Unincorporated $\alpha$-$^{32}$P CTP were removed by two consecutive precipitations with ammonium acetate/ethanol as described above. The quality of the RNA transcript was analysed by electrophoresis through a formaldehyde agarose gels as described in Sambrook et al, see above followed by autoradiography. The predominant transcripts from both plasmid templates were found to be full length.

The addition of a His$_6$ tail does not alter the hybridization properties of the PNA To determine whether the hybridization properties of a PNA oligomer are affected by the presence of an oligohistidine tag we synthesized a $His_6$-PNA (PNAD111) in which the $His_6$ motif is separated from the PNA domain by three "ado" linkers. As a control we synthesized the non-His PNA (PNAD106, without histidine residues) and the native PNA (PNAD103; without histidine residues and ado linkers). Each of the PNAs were hybridized separately to oligonucleotides containing either a complementary or a single base mismatched PNA target site and the melting temperature of each duplex ($T_m$) was determined spectrophotometrically. To mimic the situation normally encountered in hybridization experiments (i.e. probe target site is part of a large nucleic acid) the oligonucleotides were synthesized as 40mers comprising the 15 nt PNA target site in the middle. As shown in FIG. 2 neither the addition of the ado linkers nor the $His_6$ tag have any significant effect on the affinity or the specificity of the PNA. Thus, the duplexes formed between the fully complementary oligonucleotide and either of the three PNAs have essentially similar $T_m$ values. Likewise the $T_m$ values for the various single se mismatched complexes are quite similar.

Capture efficiency is affected by the number of histidine residues carried out by the PNA For optimal capture efficiency the PNA must carry sufficient histidine residues to provide tight binding to the Ni-NTA resin. To determine the number of histidine residues that would provide optimal capture, derivatives of PNAD 111 carrying from 3 to 8 histidines were synthesized and analyzed as above using the complementary, labeled 40mer oligonucleotide. As shown in FIG. 2, capture efficiencies improve up to 5 to 6 histidine residues. Increasing the number of histidine residues further to 7 or 8 does not increase the capture efficiency. Thus, the $His_6$ tag chosen originally was used in all further experiments.

$His_6$ PNA allows the selection of oligonucleotides in which the target sequence is part of an intra-molecular stem structure It has been shown previously (Nature 365, 566–568 (1993)) that the thermostability of a PNA/DNA duplex increases slightly as the ionic strength of the buffer was decreased from 100 mM to 10 mM $Na^+$. When used as a hybrid selection probe, this property of PNA is most useful as it allows hybridization under conditions of very low salt that selectively destabilize nucleic acid structures that could interfere with probe binding. The published analysis was limited to a fully complementary PA/DNA duplex and therefore did not address the question of whether the specificity of PNA/DNA duplex formation was maintained under low salt conditions. To assess this, we measure the $T_m$ values of fully matched and single base mismatched $His_6$-PNA/DNA duplexes at various salt concentrations. As shown in FIG. 3 we confirmed the previously reported increase in affinity of the fully complementary PNA/DNA duplex as the salt concentration was lowered. Thus, within the $Na_+$ concentration range employed (1 to 540 mM) we observed an increase in affinity of approx. 12° C. Similar behavior was observed with the duplexes containing single base mismatches showing that the specificity of the PNAs was retained over the entire range of ionic strength tested. To illustrate the destabilization of nucleic acid structures at similar salt conditions, FIG. 3 includes the $T_m$ values for the corresponding PNA/DNA duplexes. A a concentration of 2 mM $Na^+$ the complementary DNAs did not produce melting curves within a 10°–90° C. temperature range, indicating that no hybridization takes place.

An oligonucleotide was designed in such a way that the entire PNA target site would form one side of an intra-molecular stem structure (FIG. 4A). The labeled oligonucleotide was incubated at room temperature in the presence of the complementary $His_6$-PNA (PNAD 111) in either low salt buffer (1 mM $Na_2HPO_4$, pH 8.0, 500 mM NaCl, 0.1% Triton X-100 and 2M urea) and the selection procedure was performed as before. The results of the experiments are presented in FIG. 4B. When selection was carried out in high salt buffer (white bars) where the intra-molecular stem/loop structure should be stable the observed capture efficiency was about 3%. In contrast, the capture efficiency was approx. 56% when hybridization was carried out in the low salt buffer (black bars) where the stem/loop structure should be either very unstable or absent.

$His_6$ PNA allows selective purification of complementary oligonucleotides against a background of oligonucleotides containing single base mismatches of the PNA Selective purification of target sequences that differs by only one base pair represents the most difficult task for any hybrid selection method. To evaluate the performance of the $His_6$-PNA selection system in this context we used a mixture of oligonucleotides that were either complementary to the PNA or contained a single base mismatch or which had an entirely non-complementary sequence. A 20-fold molar excess of $His_6$-PNA was added to the mixture and hybridization was carried out for 10 min at 55° C. After the first round of selection on the Ni-NTA column, the same quantity of fresh PNA was added to one half of the eluent from the column in the run-through, wash and eluent steps were then precipitated by ethanol and analyzed by gel electrophoresis in a 16% denaturing polyacrylamide gel, followed by autoradiography. FIG. 5 shows that the majority of the non-complementary oligonucleotide (middle band) was removed in the first round of selection, indicating that non-specific binding of oligonucleotides to the column was very low. Concurrently, a substantial enrichment of complementary oligonucleotide (upper band) over the single base mismatched oligo (lower band) was achieved. Scanning of the autoradiogram indicated that approx. 72% of the complementary oligonucleotide and 7% of the single base mismatched oligonucleotide was recovered in the eluent, corresponding to a purification factor of 10. In the second round of selection the selective enrichment was further enhanced. Thus, the predominant species found in eluent II is the complementary target oligonucleotide. Again, scanning of the autoradiogram indicated that an enrichment factor of approx. 10 was obtained, corresponding to an overall purification factor of 100 in the two rounds of selection.

Large, single stranded RNAs can be selected using the $His_6$-PNA system

We analysed the relationship between capure efficiency and the size of the nucleic acid target. Labelled, run-off RNA transcripts of 257 nt. and 2224 nt. containing target sequences for different $(His)_6$-PNAs and a control 290 nt. RNA that did not contain PNA targetsited were synthesised in-vitro using linearized plasmids as template. Each of the RNAs were incubated either without $(His)_6$-PNAs, or with one or several different $(His)_6$-PNAs and selection was carried out as before. As shown in FIG. 6 essentially no RNA is captured on the column in the reactions where either the 290 nt. control RNA is used in combination with non-complementary $(His)_6$-PNAs (row 1 and 2) or where the $(His)_6$-PNAs are excluded (row 3 and 7). in contrast, specific capture is observed when the 257 nt. and 2224 nt. RNAs are incubated with the complementary $(His)_6$-PNAs. In the case of the 257 nt. RNA the observed capture efficiency is approx. 45% when using single $(His)_6$-PNAs (row 4 and 5).

The capture efficiency decreases as the size of the target RNA increases. Thus, PNAD 111 which is complementary to both RNAs is about twice as effective in selecting the 257 nt RNA (44.0%, row 4) as the 2224 nt RNA (25%, row 8). Similar differences in capture efficiencies of the 257 and 2224 nt RNA transcripts is obtained with the majority of other PNAs tested (PNAD133: row 5; PNAD113, row 9; and PNAD154, row 11). The PNAD 153 (row 10), however, is about 50% more effective in capturing the 2224 RNA transcript as compared to the other PNAs. The reason for this increased capture efficiency is unclear.

The location of the PNA target site in the RNA does not appear to affect capture efficiencies significantly. Thus, PNAD 111 (row 8) and PNAD 154 (row 11) who's target sequences are located at the end and in the middle of the 2224 RNA transcript, respectively, are equally efficient in capture and this also appllies to the two PNAs (PNAD 111, row 4 and PNAD 133, row 5) directed against the 257 nt. RNA transcript.

The size of the PNA domain in the $(His)_6$-PNA chimera does not appear to affect the capture efficiency. Thus, PNAD 111 (a 15mer PNA) is as good in selecting the 2224 nt RNA as its 5 base extended 20mer derivative, PNAD 113 (compare row 8 and 9). This suggests that the weak link in the selection procedure is either the link between the $(His)_6$ segment and the chelated $Ni^{2+}$ ion or the link between the $Ni^{2+}$ ion and the NTA molecule on the resin. This contention is supported by the finding that capture efficiencies improve when two or three $(His)_6$-PNAs are used in conjunction, thereby providing more attachment points for the PNA/RNA complex to the Ni-NTA resin. Using for instance 3 different $(His)_6$-PNAs the capture efficiency of the 2224 nt RNA increases to 64.9% (row 15) as compared to approx. 25% when using each $(His)_6$-PNA separately.

In the above description, alkyl moieties, unless otherwise specified, preferably contain 1–6, most preferred 1–3 carbon atoms. Aromatic moieties, preferably 6–14, most preferred 6–10 carbon atoms. Both alkyl moieties and aromatic moieties may be substituted or unsubstituted by groups containing heteroatoms, such as O, N or S. The alkyl moieties can be straight-chained or branched.

Preferred aromatic moieties are phenyl, imidazolyl, or pyridyl. Preferred DNA intercalators include anthraquinolyl, psoralyl or ethidium bromide.

Preferred heterocyclic moieties include piperidinyl, morpholinyl or pyrrolidinyl.

Preferred reporter ligands include biotinoyl, dioxigenoyl or fluoresceinoyl.

Preferred chealting moieties include EDTA, NTA or bispyridinoyl.

Preferred aryl groups are phenyl. Preferred aralkyl groups are tolyl. Preferred heteroaryl groups include pyrimidinyl.

Preferred alicyclic or heterocyclic groups for $R^6$ and $R^7$ include cyclohexenoyl and piperazinoyl.

Examples of groups for R' and R" are the following:

alkyl: methyl; an amino protecting group: t-butyloxycarbonyl; a reporter ligand: biotin; an intercalator: anthraquinolyl; a chelator: bispyridyl; a peptide: kemptide; a protein: alkaline phosphatase; a carbohydrate: sucrose; a lipid: cholesterol; a steroid: dioxigenin; a nucleoside: adenosin; a nucleotide: adenosine monophosphate; a nucleotide diphosphate: adenosine diphosphate; a nucleotide triphosphate: adenosine triphosphate; an oligonucleotide: $A_{10}$; a soluble polymer: dextrane; a non-soluble polymer: magnetic bead.

---

We claim:

1. A method of capturing a nucleic acid analog on a solid support, the method comprising:
  (a) contacting a nucleic acid analog, at least one chelatable metal ion and a solid support comprising a solid support moiety capable of binding the at least one chelatable metal ion, the nucleic acid analog comprising
    (1) a polymeric strand portion comprising (i) a backbone comprising a plurality of linked backbone moieties and (ii) a plurality of ligands, each of the plurality of ligands being directly or indirectly bound to at least one of the plurality of linked backbone moieties; and
    (2) a chelating moiety, attached to the polymeric strand portion, capable of binding the at least one chelatable metal ion,
    wherein the nucleic acid analog is capable of hybridizing to a nucleic acid having a complementary sequence therewith, and
  (b) capturing the nucleic acid analog on the solid support by binding (1) the chelating moiety and the at least one chelatable metal ion and (2) the at least one chelatable metal ion and the solid support moiety.

2. The method of claim 1, wherein the chelating moiety is bound to the at least one chelatable metal ion before the nucleic acid analog and the solid support are contacted.

3. The method of claim 1, wherein the at least one chelatable metal ion is bound to the solid support moiety before the nucleic acid analog and the solid support are contacted.

4. The method of claim 1, wherein the solid support further comprises agarose gel and the solid support moiety comprises aminotriacetic acid, and wherein the at least one chelatable metal ion comprises nickel.

5. The method of claim 1, wherein the at least one chelatable metal ion comprises nickel or copper.

6. The method of claim 1, wherein the solid support comprises ethylenediamine-tetraacetic acid or aminotriacetic acid.

7. The method of claim 1, wherein the solid support comprises a plurality of magnetic particles.

8. The method of claim 1, wherein, in step (a), the nucleic acid analog is present in a first volume of solution, and further comprising, after step (b), (c) separating the captured nucleic acid analog of step (b) from the first volume of solution, and (d) thereafter eluting the nucleic acid analog from the solid support in a quantity of liquid to produce a second volume of solution containing the nucleic acid analog, wherein the second volume of solution is less than the first volume of solution.

9. The method of claim 1, further comprising, after step (b), (c) hybridizing to the nucleic acid analog a nucleic acid having a sequence which is complementary to the nucleic acid analog.

10. The method of claim 1, wherein the chelating moiety is attached to the backbone at one terminus of the backbone.

11. The method of claim 1, wherein the backbone comprises a polymer selected from the group consisting of polyamide, polythioamide, polysulphinamide and polysulphonamide.

12. The method of claim 11, wherein the backbone has an N-terminus and the chelating moiety is attached to the backbone at the N-terminus of the backbone.

13. The method of claim 1, wherein the chelating moiety comprises a sequence of peptide bonded amino acids.

14. The method of claim 13, wherein the sequence of peptide bonded amino acids is selected from His-Gly-Asp and (His)$_n$, wherein n=3–10.

15. The method of claim 1, wherein the chelating moiety is capable of binding more than one metal ion.

16. The method of claim 1, wherein the chelating moiety comprises a polycarboxylic acid substituted amine.

17. The method of claim 16, wherein the chelating moiety comprises ethylenediamine-tetraacetic acid or aminotriacetic acid.

18. The method of claim 1, wherein the backbone comprises polyamide, each of the plurality of ligands is bound directly or indirectly to a nitrogen atom in the backbone, and wherein each ligand-binding nitrogen atom is separated from an adjacent ligand-binding nitrogen atom by from 4 to 8 intervening atoms in the backbone.

19. The method of claim 1, wherein the nucleic acid analog is capable of hybridizing to one strand of a double-stranded nucleic acid, the one strand comprising a sequence which is complementary to the nucleic acid analog, in such a way as to displace the other strand of the double-stranded nucleic acid from the one strand.

20. The method of claim 1, wherein the nucleic acid analog is a compound of formula 1

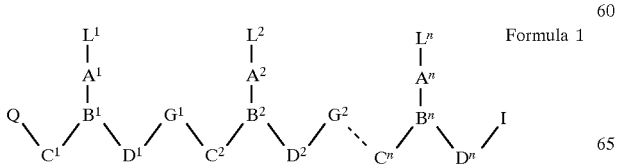

Formula 1 wherein:

n is at least 2;

each of $L^1$–$L^n$ is independently selected from the group consisting of hydrogen, hydroxy, ($C_1$–$C_4$)alkanoyl, a naturally occurring nucleobase, a non-naturally occurring nucleobase, an aromatic moiety, a DNA intercalator, a nucleobase-binding group, a heterocyclic moiety, a reporter ligand and a chelating moiety;

each of $C^1$–$C^n$ is independently selected from the group consisting of $(CR^6R^7)_y$, $(CHR^6CHR^7)_y$ and $(CR^6R^7CH_2)_y$, wherein $R^6$ is hydrogen and $R^7$ is selected from the group consisting of one of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkythio, $NR^3R^4$ and $SR^5$, wherein $R^3$ and $R^4$ are as defined below, and $R^5$ is selected from the group consisting of (a) hydrogen, (b) ($C_1$–$C_6$)alkyl, (c) hydroxy, (d) alkoxy, and (e) alkylthio-substituted ($C_1$–$C_6$)alkyl, or $R^6$ and $R^7$ taken together form an alicyclic or heterocyclic system;

each of $D^1$–$D^n$ is independently selected from the group consisting of $(CR^6R^7)_z$, $(CHR^6CHR^7)_z$ and $(CH_2CR^6R^7)_z$, wherein $R^6$ and $R^7$ are as defined above;

each of y and z is zero or an integer from 1 to 10, wherein $2 \leq y+z \leq 10$;

each of $G^1$–$G^{n-1}$ is independently selected from the group consisting of —NR$^3$CO—, —CONR$^3$—, —NR$^3$CS—, —CSNR$^3$—, —NR$^3$SO—, —SONR$^3$—, —NR$^3$SO$_2$— and —SO$_2$NR$^3$—, where $R^3$ is as defined below;

each of $A^1$–$A^n$ and $B^1$–$B^n$ are selected such that:

(a) A is selected from the group consisting of a group of formula (IIa), (IIb), (IIc) and (IId), and B is N or $R^3N^+$; or (b) A is a group of formula (IId) and B is CH;

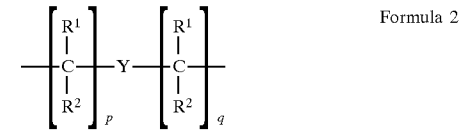

Formula 2

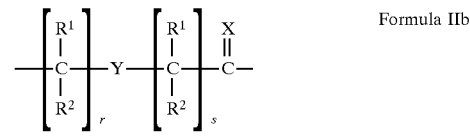

Formula IIb

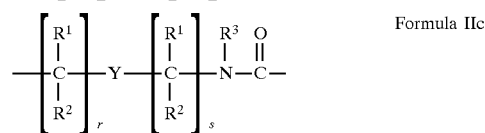

Formula IIc

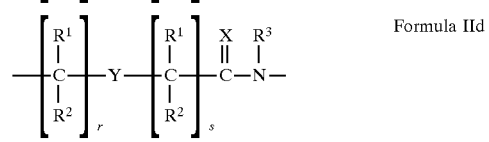

Formula IId wherein:

X is selected from the group consisting of O, S, Se, NR$^3$, CH$_2$ and C(CH$_3$)$_2$;

Y is selected from the group consisting of a single bond, O, S and NR$^4$;

each of p and q is zero or an integer from 1 to 5;

each or r and s is zero or an integer from 1 to 5;

each of $R^1$ and $R^2$ is independently selected from the group consisting of (a) hydrogen, (b) $(C_1-C_4)$alkyl which is unsubstituted or substituted by one of hydroxy-, alkoxy- and alkylthio-, (c) hydroxy, (d) alkoxy, (e) alkylthio, (f) amino and (g) halogen;

each of $R^3$ and $R^4$ is independently selected from the group consisting of (a) hydrogen, (b) $(C_1-C_4)$alkyl which is unsubstituted or substituted by one of hydroxy-, alkoxy- and alkylthio, (c) hydroxy, (d) alkoxy, (e) alkylthio and (f) amino;

I is —NR'R'" wherein R' is defined as above and —R'" is a chelating moiety.

21. The method of claim 20, wherein at least one of $L^1-L^n$ is selected from the group consisting of a naturally occurring nucleobase, a non-naturally occurring nucleobase, a DNA intercalator and a nucleobase-binding group.

22. The method of claim 20, wherein the nucleic acid analog is a compound selected from the group consisting of formula III,

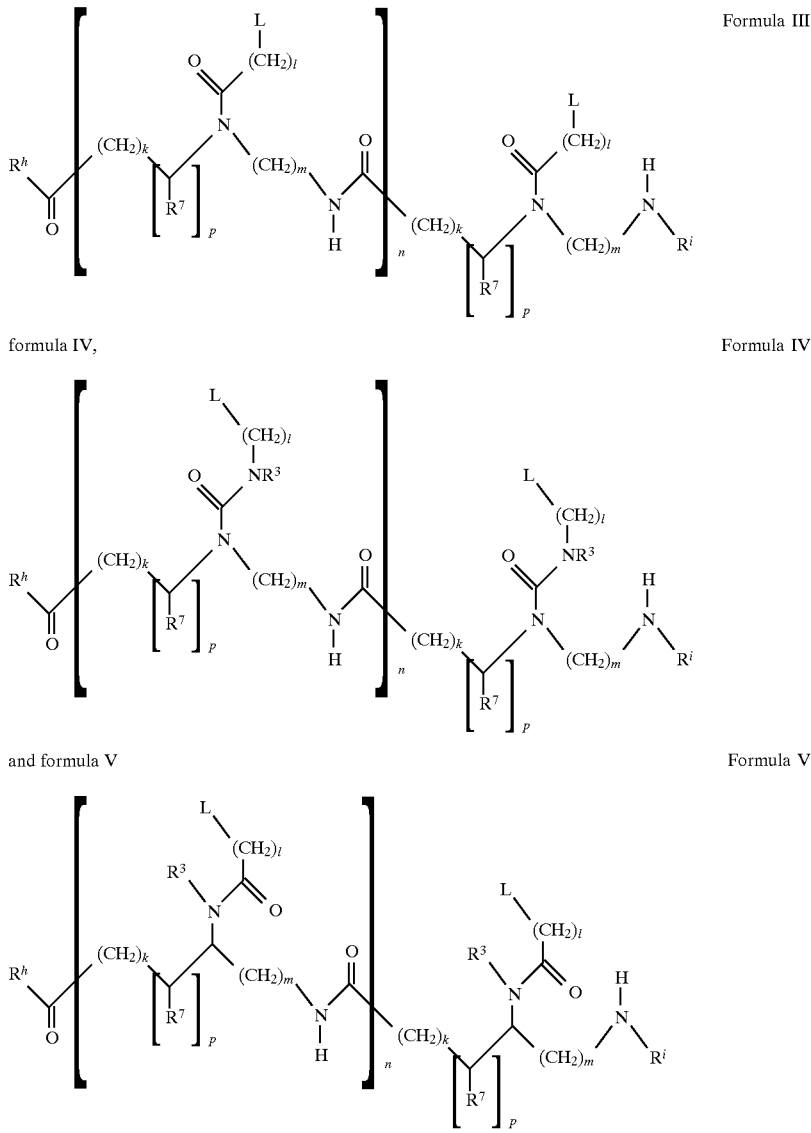

Q is selected from the group consisting of —CO$_2$H, —CONR'R", —SO$_3$H, —SO$_2$—NR'R", an activated derivative of —CO$_2$H and an activated derivative of —SO$_3$H, wherein R' and R" are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer; and wherein:
each L is independently selected from the group consisting of hydrogen, phenyl, a heterocyclic moiety, a naturally occurring nucleobase, and a non-naturally occurring nucleobase;
each $R^7$ is independently selected from the group consisting of hydrogen and one of the side chains of naturally occurring alpha amino acids;
n is an integer greater than 1,
each k, l, and m is, independently, zero or an integer from 1 to 5;

each p is zero or 1;

$R^h$ is selected from OH, $NH_2$ and —$NHLysNH_2$; and $R^i$ is a chelating moiety.

23. A method of capturing a nucleic acid on a solid support, comprising:
(a) hybridizing the nucleic acid with a nucleic acid analog to form a hybrid, the nucleic acid analog comprising
   (1) a polymeric strand portion comprising (i) a backbone comprising a plurality of linked backbone moieties and (ii) a plurality of ligands, each of the plurality of ligands being directly or indirectly bound to at least one of the plurality of linked backbone moieties; and
   (2) a chelating moiety, attached to the polymeric strand portion, capable of binding at least one chelatable metal ion;
(b) thereafter, binding the at least one chelatable metal ion and the chelating moiety to form a chelatable hybrid complex; and
(c) capturing the chelatable hybrid complex on a solid support, comprising a solid support moiety capable of binding the at least one chelatable metal ion, by binding the at least one chelatable metal ion and the solid support moiety.

24. A method of capturing a nucleic acid on a solid support, comprising:
(a) providing a nucleic acid analog comprising
   (1) a polymeric strand portion comprising (i) a backbone comprising a plurality of linked backbone moieties and (ii) a plurality of ligands, each of the plurality of ligands being directly or indirectly bound to at least one of the plurality of linked backbone moieties; and
   (2) a chelating moiety, attached to the polymeric strand portion, capable of binding at least one chelatable metal ion;
(b) thereafter, binding the at least one chelatable metal ion and the chelating moiety to form a chelatable nucleic acid analog complex;
(c) hybridizing the nucleic acid with the chelatable nucleic acid analog complex to form a hybrid; and
(d) capturing the hybrid on a solid support, comprising a solid support moiety capable of binding the at least one chelatable metal ion, by binding the at least one chelatable metal ion and the solid support moiety.

25. A method of capturing a nucleic acid on a solid support, comprising:
(a) hybridizing the nucleic acid with a nucleic acid analog to form a hybrid, the nucleic acid analog comprising
   (1) a polymeric strand portion comprising (i) a backbone comprising a plurality of linked backbone moieties and (ii) a plurality of ligands, each of the plurality of ligands being directly or indirectly bound to at least one of the plurality of linked backbone moieties; and
   (2) a chelating moiety, attached to the polymeric strand portion, capable of binding at least one chelatable metal ion; and
(b) thereafter, capturing the hybrid on a solid support, comprising the at least one chelatable metal ion, by binding the at least one chelatable metal ion and the chelating moiety.

26. A method of capturing a nucleic acid on a solid support, comprising:
(a) providing a solid support comprising a nucleic acid analog bound to the solid support by at least one chelatable metal ion, the nucleic acid analog comprising (1) a polymeric strand portion comprising (i) a backbone comprising a plurality of linked backbone moieties and (ii) a plurality of ligands, each of the plurality of ligands being directly or indirectly bound to at least one of the plurality of linked backbone moieties; and
   (2) a chelating moiety, attached to the polymeric strand portion, bound to the at least one chelatable metal ion; and
(b) thereafter, capturing the nucleic acid on the solid support by hybridizing the nucleic acid with the nucleic acid analog.

27. The method of claim 26, wherein the at least one chelatable metal ion comprises nickel or copper.

28. The method of claim 26, wherein the chelating moiety is attached to the backbone at one terminus of the backbone.

29. The method of claim 26, wherein the backbone comprises a polymer selected from the group consisting of polyamide, polythioamide, polysulphinamide and polysulphonamide.

30. The method of claim 26, wherein the backbone has an N-terminus and the chelating moiety is attached to the backbone at the N-terminus of the backbone.

31. The method of claim 26, wherein the chelating moiety comprises a sequence of peptide bonded amino acids.

32. The method of claim 31, wherein the sequence of peptide bonded amino acids is selected from His-Gly-Asp and $(His)_n$, wherein n=3–10.

33. The method of claim 26, wherein the chelating moiety comprises a polycarboxylic acid substituted amine.

34. The method of claim 33, wherein the chelating moiety comprises ethylenediamine-tetraacetic acid or aminotriacetic acid.

35. The method of claim 26, wherein the backbone comprises polyamide, each of the plurality of ligands is bound directly or indirectly to a nitrogen atom in the backbone, and wherein each ligand-binding nitrogen atom is separated from an adjacent ligand-binding nitrogen atom by from 4 to 8 intervening atoms in the backbone.

36. The method of claim 26, wherein the nucleic acid analog is capable of hybridizing to one strand of a double-stranded nucleic acid, the one strand comprising a sequence which is complementary to the nucleic acid analog, in such a way as to displace the other strand of the double-stranded nucleic acid from the one strand.

37. The method of claim 26, wherein the nucleic acid analog is a compound of formula 1

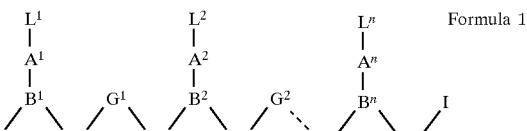

Formula 1 wherein:

n is at least 2;

each of $L^1$–$L^1$ is independently selected from the group consisting of hydrogen, hydroxy, $(C^1$–$C_4)$alkanoyl, a naturally occurring nucleobase, a non-naturally occurring nucleobase, an aromatic moiety, a DNA intercalator, a nucleobase-binding group, a heterocyclic moiety, a reporter ligand and a chelating moiety;

each of $C^1$–$C^n$ is independently selected from the group consisting of $(CR^6R^7)_y$, $(CHR^6CHR^7)_y$ and $(CR^6R^7CH_2)_y$, wherein $R^6$ is hydrogen and $R^7$ is selected from the group consisting of one of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_2-C_6)$alkoxy, $(C_1-C_6)$alkythio, $NR^3R^4$ and $SR^5$, wherein $R^3$ and $R^4$ are as defined below, and $R^5$ is selected from the group consisting of (a) hydrogen, (b) $(C_1-C_6)$alkyl, (c) hydroxy, (d) alkoxy, and (e) alkylthio-substituted $(C_1-C_6)$alkyl, or $R^6$ and $R^7$ taken together form an alicyclic or heterocyclic system;

each of $D^1-D^n$ is independently selected from the group consisting of $(CR^6R^7)_z$, $(CHR^6CHR^7)_z$ and $(CH_2CR^6R^7)_z$
wherein $R^6$ and $R^7$ are as defined above;

each of y and z is zero or an integer from 1 to 10, wherein $2 \leq y+z \leq 10$;

each of $G^1-G^{n-1}$ is independently selected from the group consisting of —$NR^3CO$—, —$CONR^3$—, —$NR^3CS$—, —$CSNR^3$—, —$NR^3SO$—, —$SONR^3$—, —$NR^3SO_2$— and —$SO_2NR^3$—, where $R^3$ is as defined below;

each of $A^1-A^n$ and $B^1-B^n$ are selected such that:
(a) A is selected from the group consisting of a group of formula (IIa), (IIb), (IIc) and (IId), and B is N or $R^3N^+$; or
(b) A is a group of formula (IId) and B is CH;

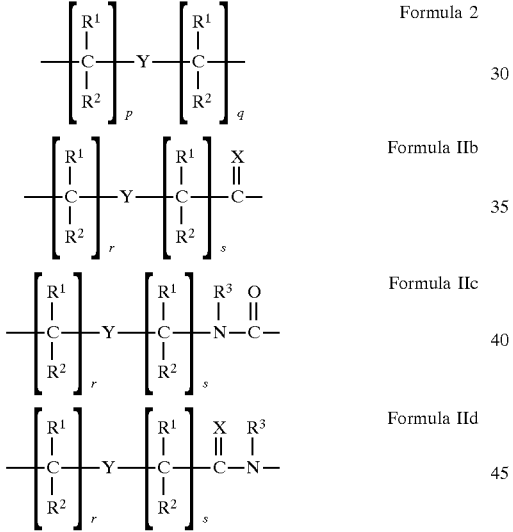

Formula 2

Formula IIb

Formula IIc

Formula IId wherein:

X is selected from the group consisting of O, S, Se, $NR^3$, $CH_2$ and $C(CH_3)_2$;

Y is selected from the group consisting of a single bond, O, S and $NR^4$;

each of p and q is zero or an integer from 1 to 5;

each or r and s is zero or an integer from 1 to 5;

each of $R^1$ and $R^2$ is independently selected from the group consisting of (a) hydrogen, (b) $(C_1-C_4)$alkyl which is unsubstituted or substituted by one of hydroxy-, alkoxy- and alkylthio-, (c) hydroxy, (d) alkoxy, (e) alkylthio, (f) amino and (g) halogen;

each of $R^3$ and $R^4$ is independently selected from the group consisting of (a) hydrogen, (b) $(C_1-C_4)$alkyl which is unsubstituted or substituted by one of hydroxy-, alkoxy- and alkylthio, (c) hydroxy, (d) alkoxy, (e) alkylthio and (f) amino;

Q is selected from the group consisting of —$CO_2H$, —$CONR'R''$, —$SO_3H$, —$SO_2$—$NR'R''$, an activated derivative of —$CO_2H$ and an activated derivative of —$SO_3H$, wherein R' and R'' are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer; and I is —NR'R''' wherein R' is defined as above and —R''' is a chelating moiety.

38. The method of claim 37, wherein at least one of $L^1-L^n$ is selected from the group consisting of a naturally occurring nucleobase, a non-naturally occurring nucleobase, a DNA intercalator and a nucleobase-binding group.

39. The method of claim 37, wherein the nucleic acid analog is a compound selected from the group consisting of formula III,

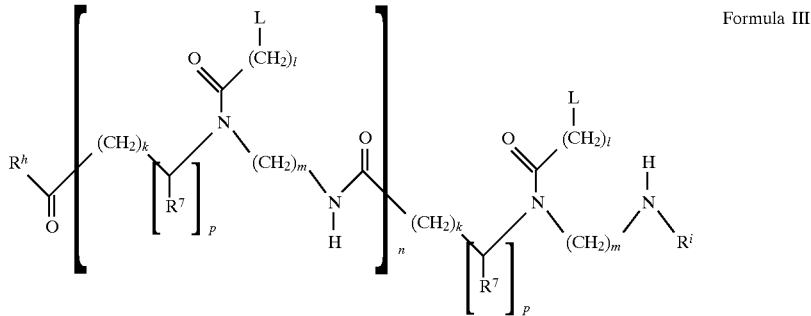

Formula III formula IV,

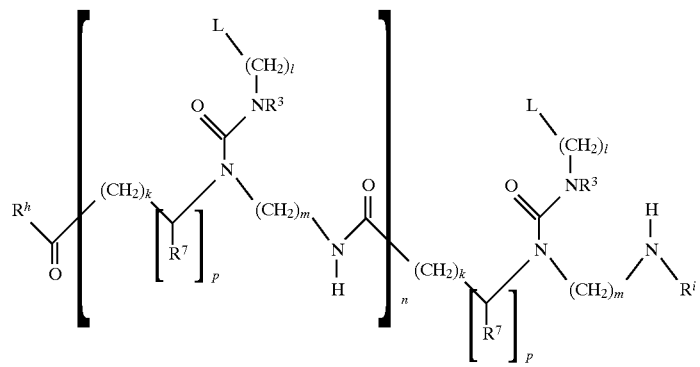

Formula IV and formula V

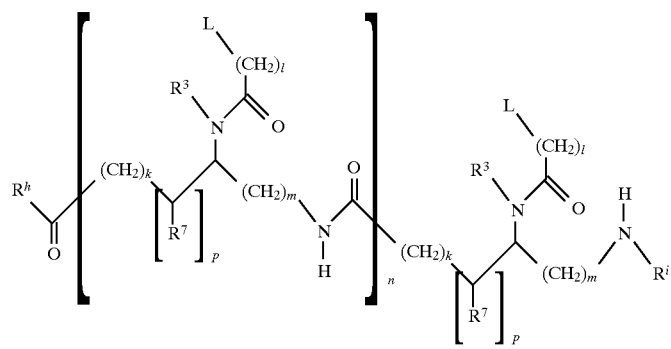

Formula V wherein:
  each L is independently selected from the group consisting of hydrogen, phenyl, a heterocyclic moiety, a naturally occurring nucleobase, and a non-naturally occurring nucleobase;
  each $R^7$ is independently selected from the group consisting of hydrogen and one of the side chains of naturally occurring alpha amino acids;
  n is an integer greater than 1,
  each k, l, and m is, independently, zero or an integer from 1 to 5;
  each p is zero or 1;
  $R^h$ is selected from OH, $NH_2$ and —$NHLysNH_2$; and
  $R^i$ is a chelating moiety.

* * * * *

UNITED STATES PATENT AND TRADEMARK OFFICE
CERTIFICATE OF CORRECTION

PATENT NO. : 5,843,663  
DATED : December 1, 1998  
INVENTOR(S) : Christopher John Stanley et al.

Page 1 of 1

It is certified that error appears in the above-identified patent and that said Letters Patent is hereby corrected as shown below:

Title page,
Change the following:
Item [73] Assignee: "Boehringer Mannheim GmbH. Mannheim, Germany" to
-- PNA Diagnostics A/S Copenhagen, Denmark --

Signed and Sealed this

Twenty-fifth Day of December, 2001

*Attest:*

JAMES E. ROGAN
*Attesting Officer*  *Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TCGAGGCAAC CGAATAGTTG TGACGTACAT TTTTTA     36

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

AGCTTAAAAA ATGTACGTCA CAACTATTCG GTTGCC     36

-continued ( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GATCCTGTAC GTCACAACTA         20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GATCTAGTTG TGACGTACAG         20

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GATCCGGCAA CCGG         14

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

AATTCCGGTT GCGG         14